(12) United States Patent
Jung, Jr.

(10) Patent No.: US 12,114,906 B2
(45) Date of Patent: Oct. 15, 2024

(54) MAPPING ASSEMBLY FOR CRYOGENIC BALLOON CATHETER SYSTEM

(71) Applicant: Boston Scientific Scimed, Inc., Maple Grove, MN (US)

(72) Inventor: Eugene J. Jung, Jr., San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 607 days.

(21) Appl. No.: 16/373,146

(22) Filed: Apr. 2, 2019

(65) Prior Publication Data

US 2019/0365451 A1 Dec. 5, 2019

Related U.S. Application Data

(60) Provisional application No. 62/680,816, filed on Jun. 5, 2018.

(51) Int. Cl.
| | |
|---|---|
| *A61B 18/02* | (2006.01) |
| *A61B 18/14* | (2006.01) |
| *A61B 18/00* | (2006.01) |
| *A61B 18/12* | (2006.01) |
| *A61B 90/00* | (2016.01) |

(52) U.S. Cl.
CPC .......... *A61B 18/02* (2013.01); *A61B 18/1492* (2013.01); *A61B 2018/00023* (2013.01); *A61B 2018/0022* (2013.01); *A61B 2018/00255* (2013.01); *A61B 2018/00351* (2013.01); *A61B 2018/00577* (2013.01); *A61B 2018/00839* (2013.01); *A61B 2018/0212* (2013.01); *A61B 2018/1266* (2013.01); *A61B 90/37* (2016.02)

(58) Field of Classification Search
CPC ................ A61B 18/02; A61B 18/1492; A61B 2018/00577; A61B 2018/0212; A61B 34/25; A61B 2018/0022; A61B 2018/00839; A61B 90/37; A61B 2018/00023; A61B 2018/00255; A61B 2018/00351; A61B 2018/1266

See application file for complete search history.

(56) References Cited

U.S. PATENT DOCUMENTS

| | | | | |
|---|---|---|---|---|
| 9,795,442 | B2* | 10/2017 | Salahieh | ............ A61B 1/00082 |
| 2007/0083194 | A1* | 4/2007 | Kunis | ................ A61B 18/1492 606/41 |

(Continued)

*Primary Examiner* — Daniel W Fowler
(74) *Attorney, Agent, or Firm* — Nelson Mullins Riley & Scarborough LLP

(57) ABSTRACT

A cryoablation catheter comprises a catheter shaft, a guidewire lumen disposed within the catheter shaft, a cryoballoon having a first end connected to the catheter shaft and an opposite second end connected to the guidewire lumen, the cryoballoon configured to transition between a deflated state and an inflated state, the cryoballoon having a maximum circumference in the inflated state, a proximal electrode array having a plurality of proximal electrodes arranged around the cryoballoon and located proximally of the maximum circumference of the cryoballoon, and a distal electrode array having a plurality of distal electrodes arranged around the cryoballoon and located distally of the maximum circumference of the cryoballoon. The cryoablation catheter has no electrodes located at the maximum circumference of the cryoballoon.

11 Claims, 8 Drawing Sheets

(56) References Cited

U.S. PATENT DOCUMENTS

| | | | |
|---|---|---|---|
| 2008/0004652 A1* | 1/2008 | Abboud | A61M 25/10181 606/192 |
| 2010/0022950 A1* | 1/2010 | Anderson | A61B 1/00114 604/100.01 |
| 2012/0143179 A1* | 6/2012 | Avitall | A61B 18/1492 606/33 |
| 2012/0296232 A1* | 11/2012 | Ng | A61B 18/1492 600/554 |
| 2013/0172877 A1* | 7/2013 | Subramaniam | A61B 18/1492 606/41 |
| 2013/0325096 A1* | 12/2013 | Dupelle | A61N 1/0496 607/142 |
| 2014/0039358 A1* | 2/2014 | Zhou | A61M 37/0092 601/3 |
| 2015/0057656 A1* | 2/2015 | Gupta | B32B 37/1292 156/60 |
| 2015/0320472 A1* | 11/2015 | Ghaffari | A61B 18/24 606/21 |
| 2016/0051321 A1* | 2/2016 | Salahieh | A61B 8/12 600/439 |
| 2016/0331459 A1* | 11/2016 | Townley | A61N 1/40 |
| 2017/0042614 A1* | 2/2017 | Salahieh | A61B 1/00082 |
| 2017/0333125 A1* | 11/2017 | Lepak | A61B 1/05 |
| 2019/0350634 A1* | 11/2019 | Jung, Jr. | A61B 5/25 |
| 2020/0077938 A1* | 3/2020 | Jung | A61B 5/4035 |
| 2020/0129220 A1* | 4/2020 | Jung | A61L 29/14 |

* cited by examiner

MAPPING ASSEMBLY FOR CRYOGENIC BALLOON CATHETER SYSTEM

CROSS-REFERENCE TO RELATED APPLICATION

This application claims priority to U.S. Provisional Application No. 62/651,385, filed on Apr. 2, 2018 and entitled "MAPPING ASSEMBLY FOR CRYOGENIC BALLOON CATHETER SYSTEM," and U.S. Provisional Application No. 62/680,816, filed on Jun. 5, 2018 and entitled "ELECTRODE ARRAY FOR BALLOON CATHETER OF INTRAVASCULAR CATHETER SYSTEM." As far as permitted, the content of U.S. Provisional Application No. 62/651,385 and U.S. Provisional Application No. 62/680,816 is incorporated in its entirety herein by reference.

TECHNICAL FIELD

The present disclosure relates to medical devices and methods for treating cardiac arrhythmias. More specifically, the disclosure relates to devices and methods for cardiac cryoablation.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few.

Catheter ablation involves delivering ablative energy to tissue inside the heart to block aberrant electrical activity from depolarizing heart muscle cells out of synchrony with the heart's normal conduction pattern. The catheter ablation procedure is performed by positioning a portion, such as a tip, of an energy delivery catheter adjacent to diseased or targeted tissue in the heart. The energy delivery component of the system is typically at or near the most distal (i.e. farthest from the operator or user) portion of the catheter, and often at the tip of the catheter. Various forms of energy are used to ablate diseased heart tissue. These can include radio frequency (RF), ultrasound and laser energy, to name a few. One form of energy that is used to ablate diseased heart tissue includes cryogenics (also referred to herein as "cryoablation"). During a cryoablation procedure, with the aid of a guidewire, the distal tip of the catheter is positioned adjacent to diseased or targeted tissue, at which time the cryogenic energy can be delivered to create tissue necrosis, rendering the ablated tissue incapable of conducting electrical signals.

Atrial fibrillation is one of the most common arrhythmias treated using cryoablation procedures. In the earliest stages of the disease, paroxysmal atrial fibrillation, the treatment strategy involves isolating the pulmonary veins from the left atrial chamber of the heart. Recently, the use of techniques known as "balloon cryotherapy" catheter procedures to treat atrial fibrillation have increased. During balloon cryotherapy, an inflatable balloon is placed inside or against an ostium of a pulmonary vein to occlude the pulmonary vein. Pulmonary vein occlusion is typically a strong indicator that complete circumferential contact is achieved between the inflatable balloon and pulmonary vein for optimal heat transfer during ablation. Some advantages of balloon cryotherapy include ease of use, shorter procedure times and improved patient outcomes. Despite these advantages, there remains needed improvement to further improve patient outcomes and to better facilitate real-time physiological monitoring of cardiac tissue.

Balloon cryotherapy to treat atrial fibrillation continues to grow due to the simplicity of the device and procedure, enabling a wide range of operators to achieve improved clinical success rates. Prior to the introduction of balloon cryotherapy, the standard practice was to use RF ablation catheters, which were almost exclusively used to perform catheter ablation to treat atrial fibrillation. RF catheters required operators with exceptional skills in directing the catheter, with a small ablative tip, to targeted cardiac tissue inside a beating heart. RF catheter operators often practice at the most advanced academic hospital systems, which in turn has limited the number of procedures performed each year. RF catheter ablations remain associated with serious, fatal or life threatening complications.

Clinical studies have demonstrated that balloon cryotherapy to treat atrial fibrillation is not inferior to RF catheter ablation. The simplicity of balloon cryotherapy has democratized the field of practice, enabling many more electrophysiologists and other cardiac specialists to perform the procedures with a high measure of success and without the complications associated with RF catheter ablations. It is believed that the balloon catheter form, with the capability to isolate the pulmonary vein with a single shot, offers superior and, possibly more durable pulmonary vein isolation. This may be due to the inflatable balloon's ability to temporarily seal the pulmonary vein of blood flow, and significantly reduce temperature effects of blood flow. Pulmonary vein occlusion can enable a more uniform delivery of energy to the ostium resulting in consistent and durable pulmonary vein isolation. It is also believed that the wide contact area of the inflatable balloon may result in wider lesions that extend to regions in the heart further away from the pulmonary vein, wherein the tissue modification of these regions can result in better clinical outcomes for the patient.

Additionally, catheter ablation of arrhythmias generally involved RF catheters adapted to both map and ablate. The mapping function was enabled via electrodes placed near or at the distal end of the catheter and were electrically connected to an external system that could display endocardial electrograms. Accordingly, the RF catheter could both map and ablate tissue using a single catheter system.

Conventional balloon cryotherapy has limitations that preclude broader application to treat more progressive stages of atrial fibrillation. Commercially available balloon catheters have not been adapted to electrically map regions inside the heart chamber, such as the left atrium. Further, the current design of balloon catheters does not enable them to isolate the pulmonary veins and areas within the left atrium, such as the posterior wall of the left atrium. In more advanced stages of atrial fibrillation, triggers are located beyond the pulmonary veins. Consequently, there remains an unmet need to both map and ablate more areas of the heart to treat advanced stages of rhythm disorders.

SUMMARY

In one example, a cryoablation catheter comprises a catheter shaft, a guidewire lumen disposed within the catheter shaft, a cryoballoon having a first end connected to the guidewire lumen and an opposite second end connected to the catheter shaft, the cryoballoon configured to transition between a deflated state and an inflated state, the cryoballoon having a maximum circumference in the inflated state, a proximal electrode array having a plurality of proximal electrodes arranged around the cryoballoon and located proximally of the maximum circumference of the cryoballoon, and a distal electrode array having a plurality of distal electrodes arranged around the cryoballoon and located distally of the maximum circumference of the cryoballoon. The cryoablation catheter has no electrodes located at the maximum circumference of the cryoballoon.

In another example, a cryoablation catheter comprising a catheter shaft, a guidewire lumen, a cryoballoon and an electrode array. The guidewire lumen is disposed within the catheter shaft, and the cryoballoon has a first end connected to the guidewire lumen and an opposite second end connected to the catheter shaft, the cryoballoon configured to transition between a deflated state and an inflated state. The electrode array includes a plurality of first flex circuits secured to the cryoballoon, each of the first flex circuits including at least three spaced apart electrodes positioned substantially equidistant from one another. The plurality of first flex circuits are arranged so that certain of the electrodes are disposed around the cryoballoon so as to define a first plane when the cryoballoon is in the inflated state, and certain other ones of the electrodes are disposed around the cryoballoon to define a second plane when the cryoballoon is in the inflated state, the first and second planes lying in a direction orthogonal to a longitudinal axis of the catheter shaft.

In another example, a method of forming a cryoablation catheter, the method comprising disposing a guidewire lumen within a catheter shaft, and attaching a plurality of first flex circuits to a distal surface of an expandable cryoballoon, each of the first flex circuits including at least three spaced apart electrodes, the electrodes being positioned substantially equidistant from one another, wherein the plurality of first flex circuits are arranged so that certain of the electrodes are disposed around the cryoballoon so as to define a first plane when the cryoballoon is in an inflated state, and certain other ones of the electrodes are disposed around the cryoballoon to define a second plane when the cryoballoon is in the inflated state, the first and second planes lying in a direction orthogonal to a longitudinal axis of the catheter shaft. The method further includes attaching a first end of the expandable cryoballoon to a distal end of the catheter shaft; and attaching a second of the cryoballoon to the guidewire lumen.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
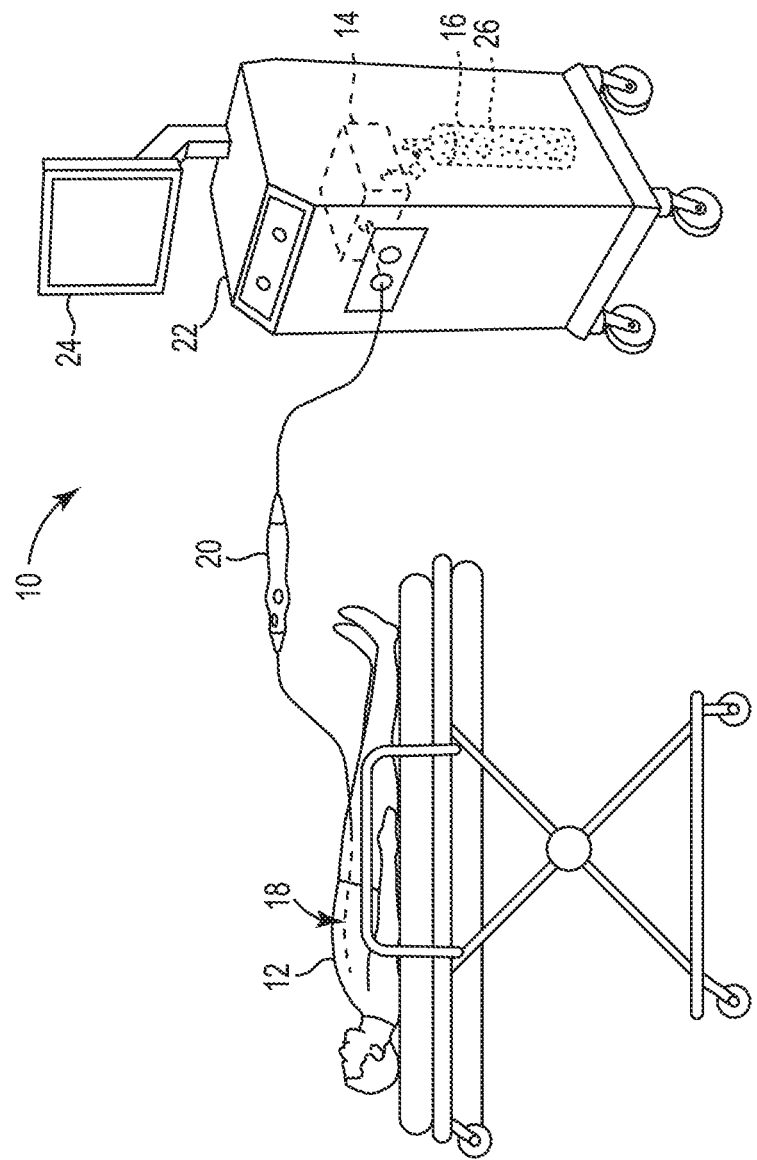
FIG. 1 is a schematic side view illustration of a patient and one embodiment of an intravascular catheter system having features of the present invention.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Embodiments of the present invention are described herein in the context of an electrode array for a balloon catheter of an intravascular catheter system. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation—specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound, laser energy and pulsed DC electric fields, as non-exclusive examples. The present invention is intended to be effective with any or all of these and other forms of energy.

FIG. 1 is a schematic view of one embodiment of an intravascular catheter system 10 (also sometimes referred to as a "catheter system") for use with a patient 12, which can be a human being or an animal. Although the catheter system 10 is specifically described herein with respect to the intravascular catheter system, it is understood and appreciated that other types of catheter systems and/or ablation systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of the intravascular catheter system is not intended to be limiting in any manner.

The design of the catheter system 10 can be varied. In certain embodiments, such as the embodiment illustrated in FIG. 1, the catheter system 10 can include one or more of a controller 14, a fluid source 16 (e.g., one or more fluid containers), a balloon catheter 18, a handle assembly 20, a control console 22 and a graphical display 24 (also sometimes referred to as a graphical user interface or "GUI"). It is understood that although FIG. 1 illustrates the structures of the catheter system 10 in a particular position, sequence and/or order, these structures can be located in any suitably different position, sequence and/or order than that illustrated in FIG. 1. It is also understood that the catheter system 10 can include fewer or additional components than those specifically illustrated and described herein.

In various embodiments, the controller 14 is configured to monitor and control the various processes of a cryoablation procedure. More specifically, the controller 14 can monitor and control release and/or retrieval of a cryogenic fluid 26 to and/or from the balloon catheter 18. The controller 14 can also control various structures that are responsible for maintaining or adjusting a flow rate and/or a pressure of the cryogenic fluid 26 that is released to the balloon catheter 18 during the cryoablation procedure. In such embodiments, the catheter system 10 delivers ablative energy in the form of cryogenic fluid 26 to cardiac tissue of the patient 12 to create tissue necrosis, rendering the ablated tissue incapable of conducting electrical signals. Additionally, in various embodiments, the controller 14 can control activation and/or deactivation of one or more other processes of the balloon catheter 18. Further, or in the alternative, the controller 14 can receive electrical signals, data and/or other information (also sometimes referred to as "sensor output") from various structures within the catheter system 10. In various embodiments, the controller 14 and the GUI 24 can be electrically connected and/or coupled. In some embodiments, the controller 14 can receive, monitor, assimilate and/or integrate any sensor output and/or any other data or information received from any structure within the catheter system 10 in order to control the operation of the balloon catheter 18. Still further, or in the alternative, the controller 14 can control positioning of portions of the balloon catheter 18 within the body of the patient 12, and/or can control any other suitable functions of the balloon catheter 18.

The fluid source 16 (also sometimes referred to as "fluid container 16") can include one or more fluid container(s) 16. It is understood that while one fluid container 16 is illustrated in FIG. 1, any suitable number of fluid containers 16 may be used. The fluid container(s) 16 can be of any suitable size, shape and/or design. The fluid container(s) 16 contains the cryogenic fluid 26, which is delivered to the balloon catheter 18 with or without input from the controller 14 during the cryoablation procedure. Once the cryoablation procedure has initiated, the cryogenic fluid 26 can be delivered and the resulting gas, after a phase change, can be retrieved from the balloon catheter 18, and can either be vented or otherwise discarded as exhaust. Additionally, the type of cryogenic fluid 26 that is used during the cryoablation procedure can vary. In one non-exclusive embodiment, the cryogenic fluid 26 can include liquid nitrous oxide. In another non-exclusive embodiment, the cryogenic fluid 26 can include liquid nitrogen. However, any other suitable cryogenic fluid 26 can be used.

The design of the balloon catheter 18 can be varied to suit the design requirements of the catheter system 10. As shown, the balloon catheter 18 is inserted into the body of the patient 12 during the cryoablation procedure. In one embodiment, the balloon catheter 18 can be positioned within the body of the patient 12 using the controller 14. Stated in another manner, the controller 14 can control positioning of the balloon catheter 18 within the body of the patient 12. Alternatively, the balloon catheter 18 can be manually positioned within the body of the patient 12 by a qualified healthcare professional (also referred to herein as an "operator"). As used herein, healthcare professional or operator can include a physician, a physician's assistant, a nurse and/or any other suitable person or individual. In certain embodiments, the balloon catheter 18 is positioned within the body of the patient 12 utilizing at least a portion of the sensor output that is received from the balloon catheter 18. For example, in various embodiments, the sensor output is received by the controller 14, which can then provide the operator with information regarding the positioning of the balloon catheter 18. Based at least partially on the sensor output feedback received by the controller 14, the operator can adjust the positioning of the balloon catheter 18 within the body of the patient 12 to ensure that the balloon catheter 18 is properly positioned relative to targeted cardiac tissue. While specific reference is made herein to the balloon catheter 18, as noted above, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the catheter system 10. In the embodiment illustrated in FIG. 1, the handle assembly 20 is separate from, but in electrical and/or fluid communication with the controller 14, the fluid container 16 and/or the graphical display 24. In some embodiments, the handle assembly 20 can integrate and/or include at least a portion of the controller 14 within an interior of the handle assembly 20. It is understood that the handle assembly 20 can include fewer or additional components than those specifically illustrated and described herein.

In the embodiment illustrated in FIG. 1, the control console 22 includes at least a portion of the controller 14, the fluid container 16 and the GUI 24. However, in alternative embodiments, the control console 22 can contain additional structures not shown or described herein. Still alternatively, the control console 22 may not include various structures that are illustrated within the control console 22 in FIG. 1. For example, in certain non-exclusive alternative embodiments, the control console 22 does not include the GUI 24.

In various embodiments, the GUI 24 is electrically connected to the controller 14. Additionally, the GUI 24 provides the operator of the catheter system 10 with information that can be used before, during and after the cryoablation procedure. For example, the GUI 24 can provide the operator with information based on the sensor output, and any other relevant information that can be used before, during and after the cryoablation procedure. The specifics of the GUI 24 can vary depending upon the design requirements of the catheter system 10, or the specific needs, specifications and/or desires of the operator.

In one embodiment, the GUI 24 can provide static visual data and/or information to the operator. In addition, or in the alternative, the GUI 24 can provide dynamic visual data and/or information to the operator, such as video data or any other data that changes over time, e.g., during the cryoablation procedure. Further, in various embodiments, the GUI 24 can include one or more colors, different sizes, varying brightness, etc., that may act as alerts to the operator. Additionally, or in the alternative, the GUI 24 can provide audio data or information to the operator.

Figure 2:
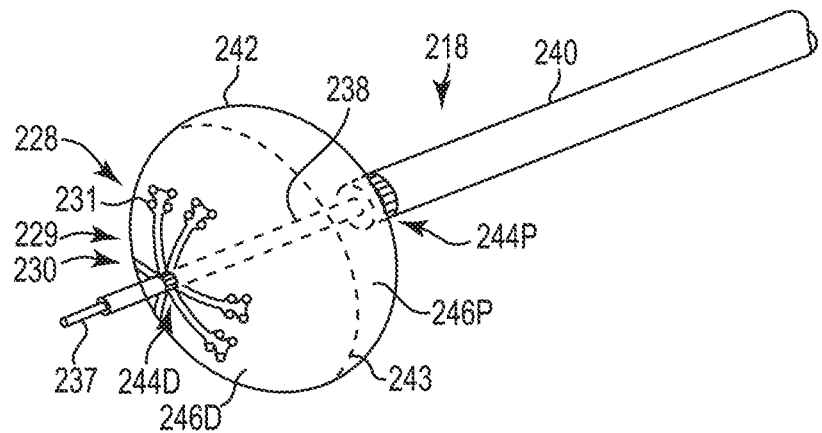
FIG. 2 is a perspective view of an embodiment of a portion of a balloon catheter including an inflatable balloon in an inflated state and a portion of an electrode array.

FIG. 2 is a perspective view of a portion of another embodiment of the catheter system 210. In the embodiment illustrated in FIG. 2, the catheter system 210 includes still another embodiment of a portion of the balloon catheter 218 in an inflated state and still another embodiment of a portion of the electrode array 228.

The balloon catheter 218 is inserted into the body of the patient 12 (illustrated in FIG. 1) during the cryoablation procedure. In this embodiment, the balloon catheter 218 includes one or more of the electrode array 228, a guidewire 237, a guidewire lumen 238, a catheter shaft 240 and an cryoballoon 242. It is understood that the balloon catheter 218 can include other structures as well that are not shown and/or described relative to FIG. 2.

The balloon catheter 218 can be positioned within the circulatory system (not shown) of the patient 12, i.e., inserted into the pulmonary vein (not shown) and/or near the ostium (not shown) of the pulmonary vein. For example, the guidewire 237 can be inserted into and/or near the pulmonary vein of the patient 12, and the guidewire lumen 238 and the catheter shaft 240 can be moved along the guidewire 237 to near the ostium of the pulmonary vein.

The cryoballoon 242 can include an inner inflatable balloon (not shown) and/or an outer cryoballoon 242. In certain embodiments, the outer cryoballoon 242 can substantially encircle and/or surround the inner inflatable balloon. Alternatively, the outer cryoballoon 242 may not have the inner inflatable balloon positioned within the interior of the outer cryoballoon 242. As referred to herein, the inner inflatable balloon and the outer cryoballoon 242 can be used interchangeably. While the inner inflatable balloon is not shown, the inner inflatable balloon and the outer cryoballoon 242 are both referred to herein as "cryoballoon 242."

During the cryoablation procedure, the cryoballoon 242 can be partially or fully inflated. As provided herein, once the cryoballoon 242 is partially or fully inflated, the cryoballoon 242 can then be properly positioned within the patient 12 to abut and/or form a seal with the relevant portion(s) of the circulatory system of the patient 12. In other words, the cryoballoon 242 is in the inflated state. In certain embodiments, when the cryoballoon 242 is fully inflated or in the inflated state, the cryoballoon 242 can include a maximum circumference 243. As used herein, the "maximum circumference 243" is the largest circumference of the cryoballoon 242 while the cryoballoon 242 is in the inflated state. Alternatively, the cryoballoon 242 can be partially or fully deflated during and/or at the completion of the cryoablation procedure.

In certain embodiments, the maximum circumference 243 can divide the cryoballoon 242 between a proximal balloon region 244P and a distal balloon region 244D. As used herein, the proximal balloon region 244P includes the region where at least a portion of the cryoballoon 242 is secured or attached to a portion of the catheter shaft 240. Further, the distal balloon region 244D includes the region where at least a portion of the cryoballoon 242 is secured or attached to the guidewire lumen 238. Alternatively, the proximal balloon region 244P and/or the distal balloon region 244D can be secured to other suitable structures within the catheter system 210. The proximal balloon region 244P and/or the distal balloon region 244D can be secured or attached to the guidewire lumen 238, the catheter shaft 240 and/or any other suitable structures, via any manner or method, such as with an adhesive or heat-bonding, as non-exclusive examples.

Additionally, in various embodiments, the cryoballoon 242 can include an inner surface and an opposed outer surface. The outer surface can include a proximal outer surface 246P and a distal outer surface 246D. The maximum circumference 243 delineates where the proximal outer surface 246P and the distal outer surface 246D meet. In other words, the maximum circumference 243 divides the outer surface. Furthermore, the inner surface can include a proximal inner surface (not shown) and a distal inner surface (not shown), which substantially corresponds with the proximal outer surface 246P and the distal outer surface 246D, respectively.

In the embodiment illustrated in FIG. 2, the electrode array 228 includes the plurality of flex circuits 229. In one embodiment, the electrode array can include six flex circuits 229. Alternatively, the electrode array 228 can include greater than six flex circuits 229 or fewer than six flex circuits 229. The positioning and/or spacing between each flex circuit 229 can vary. While the electrodes 232 (illustrated in FIGS. 2A and 2B) and conductors 234 (illustrated in FIGS. 2A and 2B) have been omitted from the flex circuits 229, it is understood that the flex circuits 229 include electrodes 232 and conductors 234. It is further understood, that the number of flex circuits 229, balloon profile, complexity and cost should be taken into consideration when determining the number of flex circuits 229 to be used in conjunction with the electrode array 228. Consideration of the number of flex circuits 229 should provide as much tissue area coverage as possible without deleteriously impacting the function or profile of the cryoballoon 242, either when the cryoballoon 242 is inflated or deflated.

At least a portion of each flex circuit 229 can extend or be routed from the handle assembly 20 and/or the controller 14 to at least a portion of the balloon catheter 218. More particularly, at least a portion of each flex circuit 229 can coupled and/or connected to the handle assembly 20 and/or the controller 14 and extend and/or be routed to the inner or outer surface of the cryoballoon 242. In FIG. 2, the mapping head 231 of each flex circuit 229 is positioned on and/or secured to the distal outer surface 246D of the cryoballoon 242.

In various embodiments, at least a portion of the flex circuits 229 can be routed through or within the guidewire lumen 238 and/or catheter shaft 240. As one non-exclusive example, at least a portion of the flex circuits 229 can be embedded within the guidewire lumen 238 and/or the catheter shaft 240, such as within a wall of the guidewire lumen 238 and/or the catheter shaft 240, for example. In another non-exclusive example, at least a portion of the flex circuits 229 can be routed through a dedicated lumen (not shown) within the guidewire lumen 238 and/or the catheter shaft 240. In still other non-exclusive examples, at least a portion of the flex circuits 229 can be positioned and/or routed on an outer surface of the guidewire lumen 238 and/or catheter shaft 240. In one embodiment, an interconnect between the flex circuits 229 and the handle assembly 20 can be covered by a polymer tubing, such as a shrink tubing, for example, when routed on the outer surface. In yet other non-exclusive examples, at least a portion of the flex circuits 229 can be positioned and/or routed on an inner surface of the guidewire lumen 238 and/or catheter shaft 240. Alternatively, the flex circuits 229 can extend from and/or be routed to the inner or outer surface of the cryoballoon 242 via any other suitable manner, configuration or combination of configurations as described above. Additionally, and/or alternatively, the flex circuits 229, or a portion thereof, can extend or be routed from, on, through and/or within any other suitable components and/or structures of the catheter system 210.

In some embodiments, if the flex circuits 229, or a portion thereof, are routed to the inner or outer surface of the cryoballoon 242 by being at least partially embedded within the guidewire lumen 238 and/or the catheter shaft 240, the flex circuits 229 can be routed through the catheter shaft 240 and a portion of the cryoballoon 242 at the proximal balloon region 244P or through the catheter shaft 240 at a location prior to or proximal to the proximal balloon region 244P. Furthermore, the flex circuits 229, or a portion thereof, can be routed through the guidewire lumen 238 and a portion of the cryoballoon 242 at the distal balloon region 244D or from the guidewire lumen 238 at a location after or distal to the distal balloon region 244D, such as out the end or tip (not shown) of the guidewire lumen. Additionally, the flex circuits 229 may also be routed through the guidewire lumen 238 and/or catheter shaft 240 as described above if the flex circuits 229, or a portion thereof, are at least partially routed to the inner or outer surface of the cryoballoon 242 through the dedicated lumen within the guidewire lumen 238 and/or the catheter shaft 240.

Additionally, as illustrated in FIG. 2, at least a portion of each flex circuit 229, i.e., the distal end 230 and/or mapping head 231, can be secured or attached to the outer surface of the cryoballoon 242. More specifically, the distal end 230 and/or mapping head 231 of each flex circuit 229 can be secured or attached to the proximal outer surface 246P and/or the distal outer surface 246D. In this configuration, the electrodes 232 can come in direct contact with a portion of the circulatory system of the patient 12, i.e., the left atrium or other parts of the heart, such as the ostium of the pulmonary vein, to better map and/or sense various physiological parameters that are occurring at or near the ostium. In alternative embodiments, the distal end 230 and/or mapping head 231 of each flex circuit 229 can be secured or attached to the inner surface of the cryoballoon 242, i.e., the proximal inner surface and/or the distal inner surface. Additionally, and/or alternatively, the distal end 230 and/or mapping head 231 of each flex circuit 229 can be secured or attached to the cryoballoon 242 via any suitable manner, such as with a flexible adhesive, by heat bonding or by using other suitable material, as non-exclusive examples.

In some embodiments, a tie layer of polymer preform can be fused onto the underside of the flex circuits 229. The tie layer can be formed from a material with a lower softening temperature and melt temperature than the cryoballoon 242. In this manner, heat applied to the flex circuits 229 can melt the tie layer to fuse it to the cryoballoon 242 without overly distorting the cryoballoon 242. The fused tie layer can be selectively heated from the surface of the flex circuit 229 until the flex circuit 229 is softened and able to bond using pressure to the surface of the cryoballoon 242. Additionally, the selection of the tie layer is predicated on having a lower softening temperature than the cryoballoon 242. Thus, the flex circuit 229 can be fused onto the surface of the cryoballoon 242 using a very thin and highly controlled amount of material on the cryoballoon 242 without distorting the shape of the cryoballoon 242. Alternatively, materials with the same softening temperature or even higher softening temperature are anticipated for use. With materials with the same softening temperature or even higher softening temperature, adjustments in the bonding pressure are made to facilitate adhesion between the tie layer and the surface of the cryoballoon 242.

It is understood that the distal end 230 and/or mapping head 231 of each flex circuit 229 secured or attached to the cryoballoon 242 can include any suitable positioning, spacing and/or configuration on the outer surface or the inner surface of the cryoballoon 242.

Figure 2A:
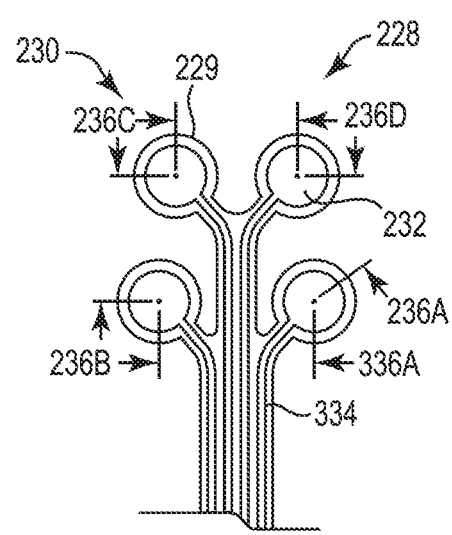
FIG. 2A is a top view of another embodiment of a portion of the balloon catheter including a portion of an electrode array.

FIG. 2A is a plan view of an embodiment of the electrode array 228 of the balloon catheter 218 of FIG. 2. In the embodiment illustrated in FIG. 2A, only one flex circuit 229 is shown. It is understood that a plurality of substantially identical flex circuits 229 or different flex circuits 229 can be included in the electrode array 228, however. The flex circuit 229 can include a proximal end (not shown) and a distal end 230. More specifically, in FIG. 3, the distal end 230 of the flex circuit 229 is illustrated. The proximal end of the flex circuit 229 can be coupled and/or connected to the handle assembly 20 (illustrated in FIG. 1) and/or the controller 14 (illustrated in FIG. 1). The distal end 230 of the flex circuit 229 is heat fused, coupled, secured and/or connected to a portion of the balloon catheter 218. Additionally, as described throughout, certain structures and/or components can be referenced as being "proximal" or "distal." As used herein, the term "proximal" means a location closer to the handle assembly 20. The term "distal" means a location further away from the handle assembly 20 than the proximal location. In some embodiments, the term "distal" can include an end or tip farthest from handle assembly 20.

While FIG. 2A illustrates a portion of one flex circuit 229, it is recognized that the electrode array 228 can include a plurality of flex circuits 229, i.e., first flex circuit, second flex circuit, third flex circuit, etc. For ease of reference, each flex circuit 229, i.e., first flex circuit, second flex circuit, third flex circuit, etc., described herein can collectively be referred to as "flex circuit(s) 229." Furthermore, the first flex circuit, second flex circuit, third flex circuit, etc. can be used interchangeably. It is further recognized that although only the distal end 230 of the flex circuit 229 is shown in FIG. 2A, the flex circuit 229 can extend from the handle assembly 20 and/or the controller 14 to at least a portion of the balloon catheter 218. For example, in some embodiments the flex circuit 229 can include a length of at least approximately 6 feet. Alternatively, the length of flex circuit 229 can be less than approximately 6 feet.

The design of the electrodes 232 can vary. The electrodes 232 can include a circular shape with identical or varying diameters. With the circular shape, the electrodes 232 can have an electrode center 235. For example, in the embodiment in FIG. 2A, the electrodes 232 can have a diameter of approximately 1 millimeter. In other embodiments, the diameter can vary to be greater or less than approximately 1 millimeter. Additionally, and/or in the alternative, the electrodes 232 can include any other suitable shape.

The design and/or configuration of the mapping head 231 can vary. As described herein, the flex circuit 229 can provide for a variety of spacing options and/or configurations of the electrodes 232 at the mapping head 231 that enables better electrocardiogram data collection.

Additionally, as described herein the electrode array 228 may include more than one or a plurality of flex circuits 229. In such instances, for example, the first flex circuit can include a first mapping head, with first electrodes, and first conductors; the second flex circuit can include a second mapping head, with second electrodes, and second conductors, etc. The mapping head 231 and electrodes 232 on each flex circuit 229 described herein can be collectively referred to as "mapping head 231" and "electrodes 232."

In the embodiment illustrated in FIG. 2A, only a portion of the flex circuit 229 is shown. Specifically, FIG. 2A shows the distal end 230 of the flex circuit 229, which also includes the mapping head 231. In the embodiment in FIG. 2A, the flex circuit 229 includes four electrodes 232. In this embodiment, the four electrodes 232 are positioned on the mapping head 231 of the flex circuit 229 to form a square configuration, wherein the electrode center 235 of each electrode 232 can define four corners of the square configuration. Together, the four electrodes 232 define a plane.

With the square configuration, the electrode spacing 236A, 236B, 236C, 236D, between the electrodes 232 can be substantially identical. In other words, the electrodes 232 can include electrode spacing 236A, 236B, 236C, 236D, between adjacent electrodes 232 from electrode center 235 to an adjacent electrode center 235 that is substantially identical. For example, the electrode spacing 236A, 236B, 236C, 236D, can include adjacent electrodes 232 that are substantially equidistant from one another, i.e., forming a square. In one embodiment, the electrode spacing 236A, 236B, 236C, 236D, between adjacent electrodes 232, i.e., from one electrode center 235 to another electrode center 235, can be approximately 2 millimeters. In alternative embodiments, the electrode spacing 236A, 236B, 236C, 236D, between adjacent electrodes 232, i.e., from one electrode center 235 to an adjacent electrode center 235 can be within a range from approximately 2 millimeters to approximately 6 millimeters or more. Alternatively, the electrode spacing 236A, 236B, 236C, 236D, from one electrode center 235 to an adjacent electrode center 235 can be less than 2 millimeters.

In some embodiments, the electrode array 228 can be limited to the balloon catheter 218. In other embodiments, the electrode array 228 can extend beyond the balloon catheter 218, i.e., be included and/or integrated with other components and/or structures of the catheter system 10. The design of the electrode array 228 can vary. In certain embodiments, the electrode array 228 includes at least one flex circuit 229. It is understood that the electrode array 228 can include fewer or additional components than those specifically illustrated and described herein.

In certain embodiments, the flex circuit 229 can reduce variations in contact resistance that sometimes results from welding electrodes 232 to conductors. Such contact resistance can have the effect of degrading electrical mapping performance. Accordingly, in various embodiments, the flex circuit 229 can be used in place of traditional subassemblies of electrodes 232 and conductors. In various embodiments, the flex circuit 229 can include at least one electrode 232 exposed at the surface for contact with tissue and at least one contiguous conductor extending from the handle assembly 20 and/or the controller 14 to at least a portion of the balloon catheter 218, all without the need for a solder joint.

The mapping head 231 includes one or more electrodes 232. In various embodiments, the mapping head 231 is positioned at the distal end 230 or tip of the flex circuit 229. The electrodes 232 can be configured to conduct and deliver electrical signals, i.e., sensor output, to tissue such as the endocardium of the heart. The sensor output can include mapping information that may be provided to the operator and/or visually displayed so that the operator can identify the positioning of the balloon catheter 218 within the body of the patient 12. Furthermore, the sensor output can include one or more physiological parameters within or outside of the pulmonary vein, such as temperature, pressure or electrical potentials within the blood of the patient 12 (illustrated in FIG. 1). In one embodiment, the electrodes 232 are in electrical communication with the controller 14, via one or more conductors.

The electrode array 228 can aid in mapping and/or ablation of cardiac tissue during the cryoablation procedure. In certain embodiments, the electrode array 228 can also sense one or more physiological parameters within or outside of a pulmonary vein (not shown) of the patient 12 (illustrated in FIG. 1), such as temperature, pressure or endocardial electrograms. Further, the electrode array 228 can provide sensor output regarding the mapping and/or the physiological parameters to the controller 14 (illustrated in FIG. 1) for storage and/or processing.

Apart from facilitating mapping during cryoablation procedures, in alternative embodiments, the electrodes 232 can be configured to deliver energy to the cardiac tissue of the patient 12. This energy can include cryoablation, RF and/or pulsed DC electroporation, as non-exclusive examples. In such embodiments, the electrodes 232 can deliver energy to cardiac tissue either sequentially after mapping or concurrently during an ablation procedure. Accordingly, the operator can ablate the tissue of the patient 12 with minimal or no movement the balloon catheter 218.

The electrodes 232 can interrogate tissue electrical activity and/or transmit electrical signals, i.e., sensor output, generated by the electrodes 232 to the controller 14. In certain embodiments, the controller 14 can be configured to process the sensor output to determine proper functioning of the catheter system 10 or positioning of the balloon catheter 218. Based on the sensor output, the controller 14 can determine that certain modifications to the functioning of the catheter system 10 are required. In one embodiment, the controller 14 can process the sensor output to determine physiological measurements, such as an endocardial electrogram.

In certain embodiments, the flex circuit 229 can include greater than one electrode 232. The flex circuit 229 can offer improved circuit density, thus enabling more electrodes 232, which can be more practically mounted on a portion of the balloon catheter 218.

In one non-exclusive embodiment, the electrodes 232 can be in electrode pairs, which may form a thermocouple, for example.

Figure 3:
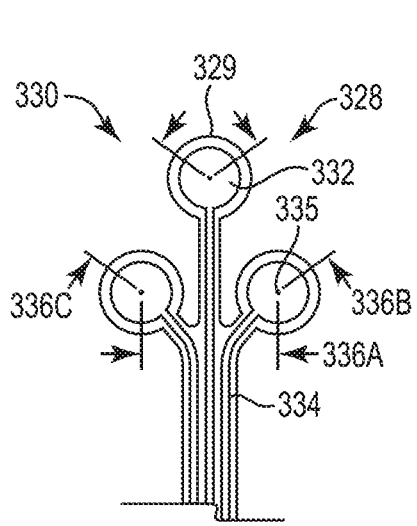
FIG. 3 is a top view of another embodiment of a portion of the balloon catheter including one embodiment of a portion of an electrode array.

FIG. 3 is a plan view of an alternative embodiment of an electrode array 338 for the balloon catheter 218 of FIG. 2. Like the electrode array 238 of FIG. 2A, the electrode array 328 can aid in mapping and/or ablation of cardiac tissue during the cryoablation procedure. In certain embodiments, the electrode array 328 can also sense one or more physiological parameters within or outside of a pulmonary vein (not shown) of the patient 12 (illustrated in FIG. 1), such as temperature, pressure or endocardial electrograms. Further, the electrode array 328 can provide sensor output regarding the mapping and/or the physiological parameters to the controller 14 (illustrated in FIG. 1) for storage and/or processing.

As shown, the electrode array 328 includes a flex circuit 329 having a distal end 330 including a mapping head 331, which in turn includes one or more electrodes 332, and conductors 334. Stated another way, the flex circuit 329 includes and or integrates the mapping head 331 having one or more electrodes 332, and one or more conductors 334, as one component. It is also understood that the flex circuit 329 can include fewer or additional components than those specifically illustrated and described herein.

Additionally, as described herein the electrode array 328 may include more than one or a plurality of flex circuits 329. In such instances, for example, the first flex circuit can include a first mapping head, with first electrodes, and first conductors; the second flex circuit can include a second mapping head, with second electrodes, and second conductors, etc. The mapping head 331, electrodes 332 and conductors 234 on each flex circuit 329 described herein can be collectively referred to as "mapping head 331," "electrodes 332" and/or "conductors 234."

Generally speaking, the design of the electrode array 328, the flex circuit 329 and/or the mapping head 330 can be substantially the same as the corresponding components of the electrode array 228 described above in connection with FIG. 2A. The electrode array 328 and mapping head 331 differ from the embodiment of FIG. 2A in that in the embodiment in FIG. 3, the electrodes 332 can be positioned on the mapping head 331 of the flex circuit 329 to form a somewhat triangular configuration or geometry. In this embodiment, the electrode center 335 of each electrode 332 can define a corner of the triangle. Together, the three electrodes 332 define a plane. In other non-exclusive embodiments, the electrodes 332 can be positioned to form any other suitable configuration or geometry, such as a different polygonal or circular shape.

The spacing between the electrodes 332 at the mapping head 331 can also vary. For example, in FIG. 3, the electrodes 332 can be substantially equidistant from one another. As used herein, use of the term "substantially" is intended to allow for minor manufacturing deviations. More specifically, in this embodiment, the electrodes 332 can include electrode spacing 336A, 336B, 336C, from electrode center 335 to electrode center 335 that is substantially identical. In other words, the electrode spacing 336A, 336B, 336C, includes electrodes 332 that are substantially equidistant from one another, i.e., forming an equilateral triangle. In one embodiment, the electrode spacing 336A, 336B, 336C, between electrodes 332, i.e., from one electrode center 335 to another electrode center 335, can be approximately 2 millimeters. Alternatively, the electrode spacing 336A, 336B, 336C between electrodes 332, i.e., from one electrode center 335 to another electrode center 335, can vary within a range from approximately 2 millimeters to 6 millimeters or more. Additionally, and/or in the alternative, the electrodes 332 may not be equidistant from one another, but may include random or varying electrode spacing 336A, 336B, 336C.

Apart from facilitating mapping during cryoablation procedures, in alternative embodiments, the electrodes 332 can be configured to deliver energy to the cardiac tissue of the patient 12. This energy can include cryoablation, RF and/or pulsed DC electroporation, as non-exclusive examples. In such embodiments, the electrodes 332 can deliver energy to cardiac tissue either sequentially after mapping or concurrently during an ablation procedure. Accordingly, the operator can ablate the tissue of the patient 12 with minimal or no movement the balloon catheter 218.

The conductors 334 can interrogate tissue electrical activity and/or transmit electrical signals, i.e., sensor output, generated by the electrodes 332 to the controller 14. In various embodiments, the conductors 334 are connected to the electrodes 332, the controller 14, and/or other components. In certain embodiments, the controller 14 can be configured to process the sensor output to determine proper functioning of the catheter system 10 or positioning of the balloon catheter 218. Based on the sensor output, the controller 14 can determine that certain modifications to the functioning of the catheter system 10 are required. In one embodiment, the controller 14 can process the sensor output to determine physiological measurements, such as an endocardial electrogram.

In certain embodiments, the flex circuit 329 can include greater than one electrode 332 and one conductor 334. The flex circuit 329 can offer improved circuit density, thus enabling more electrodes 332, which can be more practically mounted on a portion of the balloon catheter 218. More specifically, in some embodiments, such as the embodiments illustrated in FIGS. 2A and 2B, the number of electrodes 332 per flex circuit 329 can include three electrodes 332 or four electrodes 332, respectively. While FIG. 3 shows three electrodes 332 and three conductors 334, with each electrode 332 being connected to one conductor 334, it is recognized that the flex circuit 329 can include any suitable number, spacing or combination of electrodes 332 and/or conductors 334. In one non-exclusive embodiment, the electrodes 332 can be in electrode pairs, which may form a thermocouple, for example.

Figure 4A:
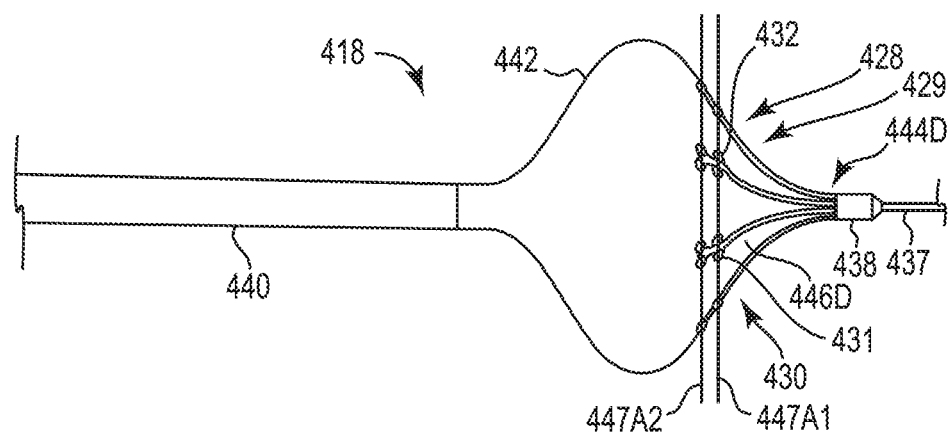
FIG. 4A is a side view of another embodiment of a portion of the balloon catheter including the inflatable balloon in the inflated state and a portion of the electrode array.

FIG. 4A is a side view of yet another embodiment of a portion of the balloon catheter 418 including the cryoballoon 442 in the inflated state and yet another embodiment of a portion of the electrode array 428. In this embodiment, the balloon catheter 418 includes the electrode array 428, the guidewire 437, the guidewire lumen 438, the catheter shaft 440 and the cryoballoon 442.

In various embodiments, such as the embodiment illustrated in FIG. 4A, the electrode array 428 can include the plurality of flex circuits 429. In FIG. 4A, the mapping head 431 of each flex circuit 429 includes the somewhat square configuration described in FIG. 2A. In this embodiment, the electrode array 428 can include flex circuits 429 where the electrodes 432 positioned on the mapping head 431 form similar configurations. Alternatively, the electrode array can include flex circuits 429 where the electrodes 432 positioned on the mapping head 431 form the same and/or varying configurations. Further, in this embodiment, the conductors 234 (illustrated in FIG. 2A) have been omitted. However, it is understood that each flex circuit 429 includes conductors 234. Additionally, in FIG. 4A, the flex circuits 429 can be routed through the guidewire lumen 438 and a portion of the cryoballoon 442 at the distal balloon region 444D with the distal end 430 and/or mapping head 431 of each flex circuit 429 being positioned on and/or secured to the distal outer surface 446D of the cryoballoon 442.

The positioning, spacing and/or configuration of the distal end 430 and/or mapping head 431 of each flex circuit 429 on the distal outer surface 446D of the cryoballoon 442 can vary. In the embodiment illustrated in FIG. 4B, the distal end 430 and/or mapping head 431 of each flex circuit 429 is positioned, spaced or secured to the distal outer surface 446D of the cryoballoon 442 such that the electrodes 432 define at least one plane 447A1, 447A2. More specifically, in FIG. 4A, the electrodes 432 at the distal end 430 and/or mapping head 431 of each flex circuit 429 can define two planes 447A1, 447A2, a first plane 447A1 and a second plane 447A2. As referred to herein, the first plane 447A1 and the second plane 447A2 can be used interchangeably. Furthermore, while FIG. 4A illustrates the two planes 447A1, 447A2 defined by the electrodes 432 on the mapping head 431 of each flex circuit 429, it is recognized that the electrodes 432 can define a plurality of planes. For ease of reference, each plane, i.e., first plane, second plane, etc., described herein can collectively be referred to as a "plane."

Additionally, in the embodiment illustrated in FIG. 4A, with the influence of the curved surface of the cryoballoon 442 being neglected, the mapping head 431 of each flex circuit 429 includes a linear configuration. More specifically, the electrodes 332 positioned on the mapping head 431 of each flex circuit 429 also include the linear configuration.

Figure 4B:
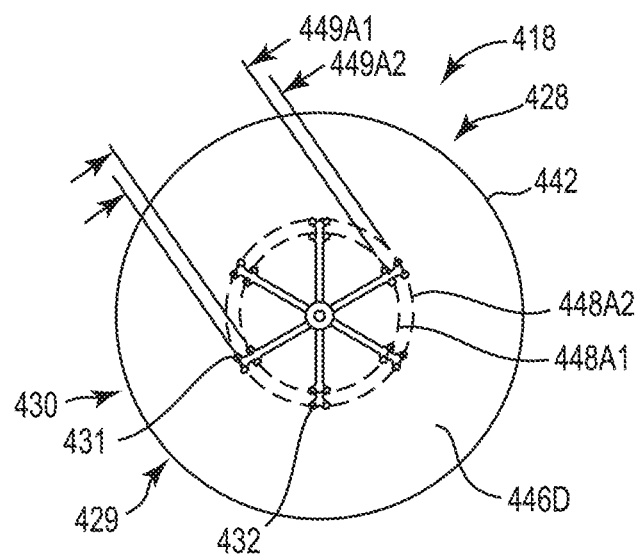
FIG. 4B is a front view of the portion of the balloon catheter including the inflatable balloon and the portion of the electrode array illustrated in FIG. 4A.

FIG. 4B is a front view of the portion of the balloon catheter 418 including the cryoballoon 442 and the portion of the electrode array 428 illustrated in FIG. 4A. More specifically, FIG. 4B illustrates the positioning, spacing and/or configuration of the distal end 430 and/or mapping head 431 of each of the plurality of flex circuits 429 secured to the distal outer surface 446D of the cryoballoon 442.

In some embodiments, such as the embodiment illustrated in FIG. 4B, the electrodes 432 within each plane 447A1, 447A2 (illustrated in FIG. 4A) can be positioned to form a somewhat circular configuration. Alternatively, the configuration or geometric shape defined by the electrodes 432 within each plane 447A1, 447A2 can vary. In certain embodiments, such as in FIG. 4B, the somewhat circular configuration can include a somewhat circular circumference 448A1, 448A2, i.e., a first somewhat circular circumference 448A1 within the first plane 447A1 and a second somewhat circular circumference 448A2 within the second plane 447A2. The somewhat circular configuration within each plane 447A1, 447A2 can also include diameters 449A1, 449A2, i.e. a first diameter 449A1 within the first plane 447A1 and a second diameter 449A2 within the second plane 447A2. Both the somewhat circular circumferences 448A1, 448A2 and diameters 449A1, 449A2 can vary or differ depending on the positioning, spacing and/or configuration of the distal end 430 and/or mapping head 431 of each flex circuit 429 on the distal outer surface 446D of the cryoballoon 442. For example, in FIG. 4B, the second somewhat circular circumference 448A2 of the second plane 447A2 can be greater than the first somewhat circular circumference 448A1 of the first plane 447A1. Alternatively, the second diameter 449A2 of the second plane 447A2 can be greater than the first diameter 449A1 of the first plane 447A1. With this configuration, the electrode array 428 can provide more precise planar mapping of endocardial heart tissue, which can allow for a clearer and more accurate tissue assessment within the boundaries of the electrodes 432 on each mapping head 431 and/or between each flex circuit 429.

Figure 5A:
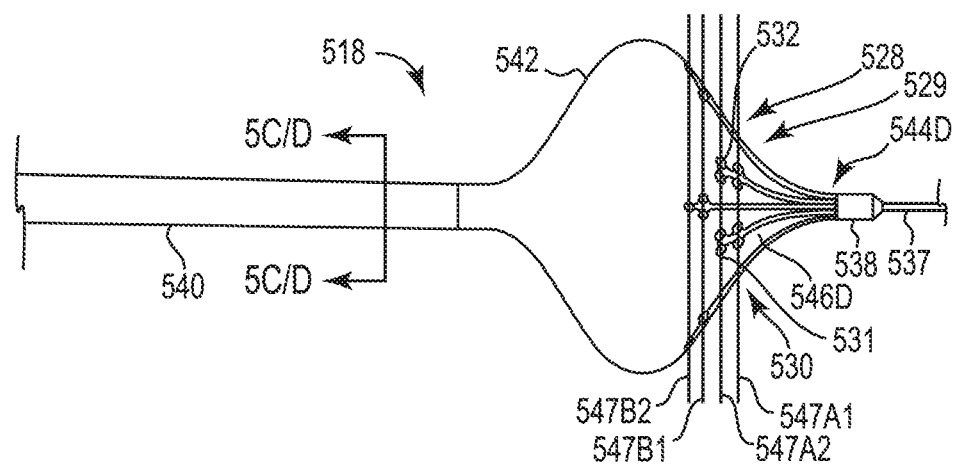
FIG. 5A is a side view of another embodiment of a portion of the balloon catheter including the inflatable balloon in the inflated state and a portion of the electrode array.

FIG. 5A is a side view of even another embodiment of a portion of the balloon catheter 518 including the cryoballoon 542 in the inflated state and even another embodiment of a portion of the electrode array 528. In FIG. 5A, the balloon catheter 518 includes the electrode array 528, the guidewire 537, the guidewire lumen 538, the catheter shaft 540 and the cryoballoon 542.

In various embodiments, such as the embodiment illustrated in FIG. 5A, the electrode array 528 includes the plurality of flex circuits 529. In FIG. 5A, the mapping head 531 of each flex circuit 529 includes the somewhat triangular and square configurations described in FIGS. 2A and 2B. In this embodiment, the electrode array 528 can include flex circuits 529 where the electrodes 532 positioned on the mapping head 531 form varying configurations. In this embodiment, the conductors 234 (illustrated in FIGS. 2A and 2B) have been omitted. However, it is understood that the flex circuits 529 include conductors 234. Additionally, in FIG. 5A, the flex circuits 529 are routed through the guidewire lumen 538 and a portion of the cryoballoon 542 at the distal balloon region 544D with the distal end 530 and/or mapping head 531 of each flex circuit 529 being positioned on and/or secured to the distal outer surface 546D of the cryoballoon 542.

In the embodiment illustrated in FIG. 5A, the electrode array 528 includes eight flex circuits 529. In this embodiment, the distal end 530 and/or mapping head 531 of each flex circuit 529 is alternatingly positioned, spaced or secured to the distal outer surface 546D of the cryoballoon 542 such that the electrodes 532 define at least one plane 547A1, 547A2, 547B1, 547B2. More specifically, in FIG. 5B, the electrodes 532 at the distal end 530 and/or mapping head 531 of each flex circuit 529 can define four planes 547A1, 547A2, 547B1, 547B2 in the direction generally orthogonal to the longitudinal axis of the catheter shaft 540.

Additionally, in the embodiment illustrated in FIG. 5A, with the influence of the curved surface of the cryoballoon 542 being neglected, the mapping head 531 of the flex circuits 529 of this non-exclusive example can include a staggered or zigzag configuration. More specifically, the electrodes 532 positioned on the mapping head 531 of the flex circuits 529 can also include the staggered or zigzag configuration.

Figure 5B:
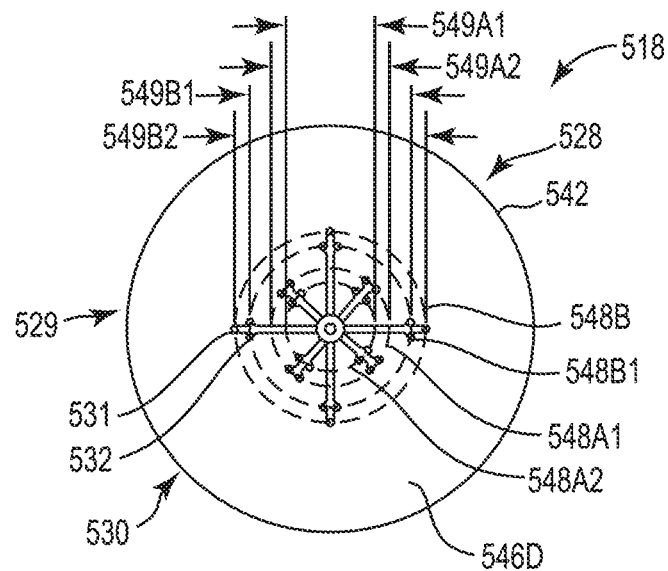
FIG. 5B is a front view of the portion of the balloon catheter including the inflatable balloon and the portion of the electrode array illustrated in FIG. 5A.

FIG. 5B is a front view of the portion of the balloon catheter 518 including the cryoballoon 542 and the portion of the electrode array 528 in FIG. 5A. More specifically, FIG. 5B illustrates the positioning, spacing and/or configuration of the distal end 530 and/or mapping head 531 of the plurality of flex circuits 529 secured to the distal outer surface 546D of the cryoballoon 542.

In some embodiments, such as the embodiment illustrated in FIG. 5B, the electrodes 532 within each plane 547A1, 547A2, 547B1, 547B2 can be positioned to form the somewhat circular configuration. In various embodiments, the somewhat circular configuration of the four planes 547A1, 547A2, 547B1, 547B2 can include the somewhat circular circumferences 548A1, 548A2, 548B1, 548B2 that vary or differ. The somewhat circular configuration can also include the diameters 549A1, 549A2, 549B1, 549B2 that vary or differ. The somewhat circular circumferences 548A1, 548A2, 548B1, 548B2 and the diameters 549A1, 549A2, 549B1, 549B2 of each plane 547A1, 547A2, 547B1, 547B2 can vary or differ depending on the positioning, spacing and/or configuration of the distal end 530 and/or mapping head 531 of each flex circuit 529 secured to the distal outer surface 546D of the cryoballoon 542.

In FIG. 5B, the somewhat circular circumferences 548A1, 548A2, 548B1, 548B2 of each of the four planes 547A1, 547A2, 547B1, 547B2 include corresponding diameters 549A1, 549A2, 549B1, 549B2 that vary or differ. For example, in this embodiment, the somewhat circular circumference 548B2 is greater than somewhat circular circumference 548B1; the somewhat circular circumference 548B1 is greater than the somewhat circular circumference 548A2; and the somewhat circular circumference 548A2 is greater than the somewhat circular circumference 548A1. Further, in this embodiment, the diameter 549B2 is greater than the diameter 549B1; the diameter 549B1 is greater than the diameter 549A2; and the diameter 549A2 is greater than the diameter 549A1.

Figure 5C:
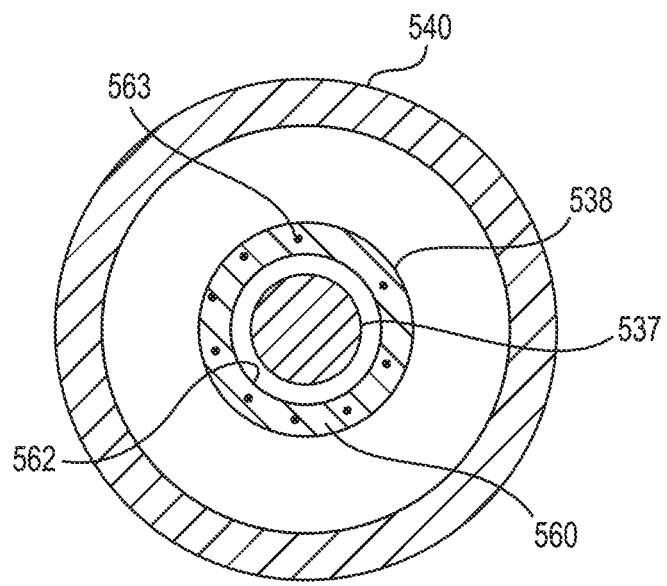
FIGS. 5C and 5D, respectively, are cross-sectional views of alternative embodiments of a portion of the balloon catheter of FIGS. 5A and 5B taken on line 5C/D-5C/D in FIG. 5A.
Figure 5D:
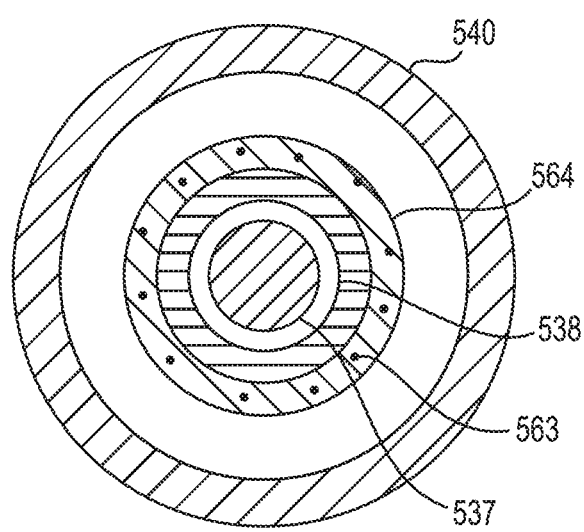

FIGS. 5C and 5D, respectively, are cross-sectional views of alternative embodiments of a portion of the balloon catheter 518 of FIGS. 5A and 5B taken on line 5C/D-5C/D in FIG. 5A. As shown in FIG. 5C, the guidewire lumen 538 receives the guidewire 537 and includes a guidewire lumen wall 560 defining a guidewire lumen inner surface 562. As further shown, a plurality of conductors 563 are routed within the guidewire lumen wall 560. The conductors 560 can extend within the guidewire lumen wall 560 and be operatively and electrically connected to the various flex circuits of the electrode array 528 (see FIGS. 5A-5B). In embodiments, the conductors 563 are integrally formed into the respective flex circuits as integral structures. Alternatively, the conductors 563 can be conductive wires, ribbons, and the like that are electrically and operatively connected to respective flex circuits proximate the cryoballoon 542.

In other embodiments, the conductors 563 can be routed along the guidewire lumen inner surface 562, or the opposed outer surface.

The alternative embodiment of FIG. 5D further includes a separate conductor lumen 564 positioned about the guidewire lumen 538. As shown, in this embodiment, the conductors 563 can be routed within the wall defining the conductor lumen 564, and otherwise configured as described with respect to FIG. 5C. In another embodiment, the conductors 563 can be routed along an outer surface of the conductor lumen 564.

Figure 6A:
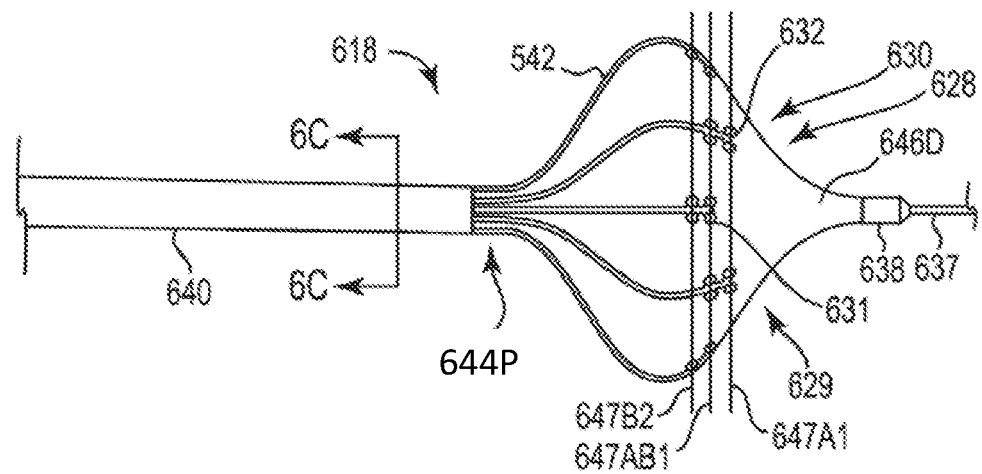
FIG. 6A is a side view of another embodiment of a portion of the balloon catheter including the inflatable balloon in the inflated state and a portion of the electrode array.

FIG. 6A is a side view of an additional embodiment of a portion of the balloon catheter 618 including the cryoballoon 642 in the inflated state and an additional embodiment of a portion of the electrode array 628. In FIG. 6A, the balloon catheter 618 includes the electrode array 628, the guidewire 637, the guidewire lumen 638, the catheter shaft 640 and the cryoballoon 642.

In various embodiments, the electrode array 628 includes the plurality of flex circuits 629. In the embodiment illustrated in FIG. 6A, the mapping head 631 of the plurality of flex circuits 629 includes the somewhat square configuration described in FIG. 2A. In this embodiment, the conductors 234 (illustrated in FIG. 2A) have been omitted. However, it is understood that each flex circuit 629 includes conductors 234. Additionally, in FIG. 6A, the flex circuits 629 routed through the catheter shaft 640 and a portion of the cryoballoon 642 at the proximal balloon region 644P with the distal end 630 and/or mapping head 631 of each flex circuit 629 being positioned on and/or secured to the distal outer surface 646D of the cryoballoon 642.

In the embodiment illustrated in FIG. 6A, the electrode array 628 includes eight flex circuits 629. In this embodiment, the distal end 630 and/or mapping head 631 of each flex circuit 629 is alternatingly positioned, spaced or secured to the distal outer surface 646D of the cryoballoon 642 such that the electrodes 632 define at least one plane 647A1, 647A2B1, 647B2. More specifically, in FIG. 6A, the electrodes 632 at the distal end 630 and/or mapping head 631 of each flex circuit 629 can define three planes 647A1, 647A2B1, 647B2. However, in this embodiment, certain electrodes 632 of neighboring flex circuits 629 can define and/or share the same plane 647A2B1.

In the embodiment illustrated in FIG. 6A, with the influence of the curved surface of the cryoballoon 642 is neglected, the mapping head 631 of the plurality of flex circuits 629 would include the staggered or zigzag configuration. More specifically, the electrodes 632 positioned on the mapping head 631 of the plurality of flex circuits 629 would include the staggered or zigzag configuration.

Figure 6B:
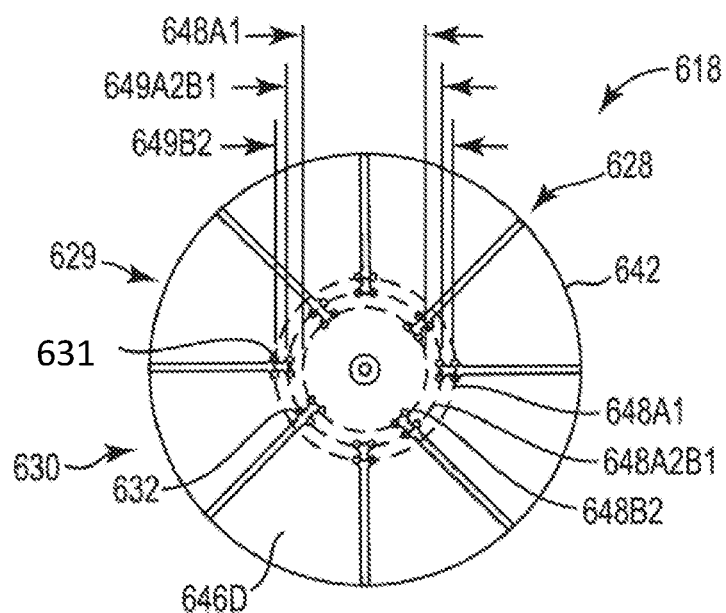
FIG. 6B is a front view of the portion of the balloon catheter including the inflatable balloon and the portion of the electrode array illustrated in FIG. 6A.

FIG. 6B is a front view of the portion of the balloon catheter 618 including the cryoballoon 642 and the portion of the electrode array 628 in FIG. 6A. More specifically, FIG. 6B illustrates the positioning, spacing and/or configuration of the distal end 630 and/or mapping head 631 of the plurality of flex circuits 629 secured to the distal outer surface 646D of the cryoballoon 642.

In some embodiments, such as the embodiment illustrated in FIG. 6B, the electrodes 632 within each plane 647A1, 647A2B1, 647B2 can be positioned to form the somewhat circular configuration. In various embodiments, the somewhat circular configuration of the three planes 647A1, 647A2B1, 647B2 can include the somewhat circular circumferences 648A1, 648A2B1, 648B2 that vary or differ. The somewhat circular configuration can also include the diameters 649A1, 649A2B1, 649B2 that vary or differ. The somewhat circular circumferences 648A1, 648A2B1, 648B2 and the diameters 649A1, 649A2B1, 649B2 of each plane 647A1, 647A2B1, 647B2 can vary or differ depending on the positioning, spacing and/or configuration of the distal end 630 and/or mapping head 631 of each flex circuit 629 secured to the distal outer surface 646D of the cryoballoon 642.

In FIG. 6B, the somewhat circular circumferences 648A1, 648A2B1, 648B2 of each of the three planes 647A1, 647A2B1, 647B2 include corresponding diameters 649A1, 649A2B1, 649B2 that vary or differ. For example, in this embodiment, the somewhat circular circumference 648B2 is greater than somewhat circular circumference 648A2B1; and the somewhat circular circumference 648A2B1 is greater than the somewhat circular circumference 648A2. Further, in this embodiment, the diameter 649B2 is greater than the diameter 649A2B1; and the diameter 649A2B1 is greater than the diameter 649A2.

Figure 6C:
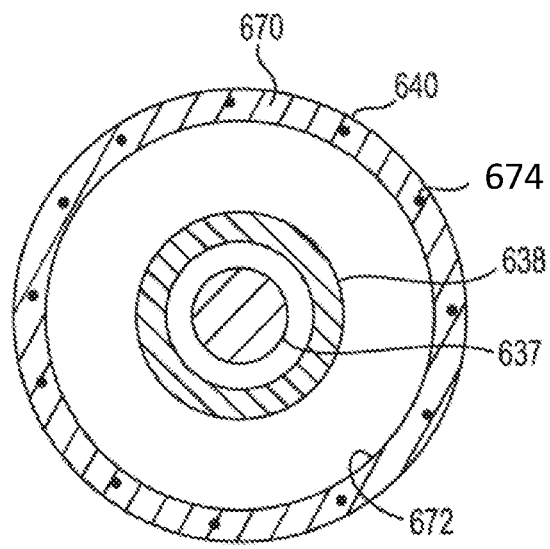
FIG. 6C a cross-sectional view of a portion of the cryogenic balloon catheter of FIGS. 6A-6B taken along the line 6C-6C in FIG. 6A.

FIG. 6C a cross-sectional view of a portion of the cryogenic balloon catheter 618 taken along the line 6C-6C in FIG. 6A. As shown, the guidewire lumen 638 receives the guidewire 637, and the catheter shaft 640 has a shaft wall 670 defining a shaft inner surface 672. As further shown, the balloon catheter 618 includes a plurality of conductors 674 associated with the shaft 640.

Generally speaking, the conductors 674 can extend or be routed from the handle assembly 20 (illustrated in FIG. 1) and/or the control system 14 to the electrode array 628, respectively, and consequently, to the electrodes 632. In the embodiment of FIG. 6C the conductors 674 can be embedded within the shaft wall 670. In other embodiments, the conductors 674 can be disposed and/or attached to the shaft inner surface 672, or to the opposite outer surface of the shaft wall 670. Still other techniques for routing the conductors 674 to the electrode array 628 will be apparent to the skilled artisan based on the foregoing.

Figure 7:
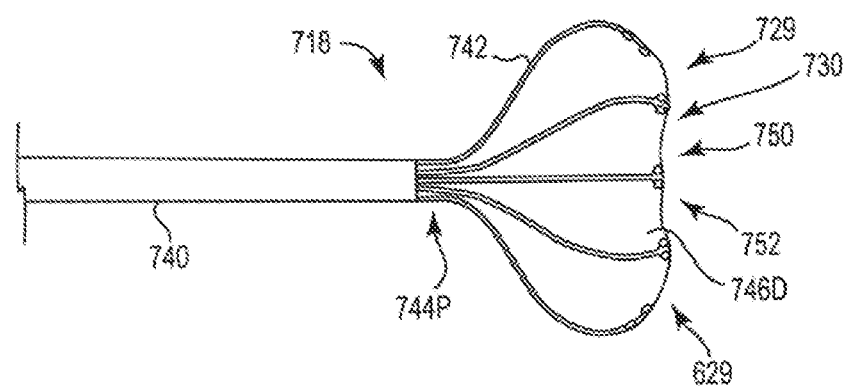
FIG. 7 is a side view of another embodiment of a portion of the balloon catheter including the inflatable balloon in a retracted state and a portion of the electrode array.

FIG. 7 is a side view of another embodiment of a portion of the balloon catheter 718 including the cryoballoon 742 in a retracted position and a portion of the electrode array 728. The retracted position can include the balloon catheter 718 that is amenable to retraction to form a distal catheter end 750 with a very small or even non-existent distal tip 752, thereby allowing the cryoballoon 742 to move to the retracted position. This type of balloon catheter 718 is sometimes referred to as a "tipless balloon catheter 718." The retracted cryoballoon 742 can more easily maneuver around left atrial anatomy, and can better comply with and/or match the left atrial anatomy (or other locations in and around the heart) compared with another type of balloon catheter 718 that cannot move to the retracted position, as the added length of the distal tip 752 would otherwise make the balloon catheter 718 difficult to position and move within the left atrium of the heart. In various embodiments, the reduction and/or elimination of the distal tip 752 and/or the distal catheter end 750 enables treatment at sites other than the pulmonary veins where the distal tip 752 would inhibit contact between the cryoballoon 742 and cardiac tissue of the patient 12 (illustrated in FIG. 1).

Additionally, in FIG. 7, the flex circuits 729 can be routed through the catheter shaft 740 and a portion of the cryoballoon 742 at the proximal balloon region 744P with the distal end 730 of each flex circuit 729 being positioned on and/or secured to the distal outer surface 746D of the retracted cryoballoon 742. However, it is understood that the tipless balloon catheter 718 and/or retracted cryoballoon 742 can include any variety of routing options, spacing options and/or configurations of the electrode array 728, the flex circuits 729 and/or the electrodes 332 (as illustrated in FIGS. 2A and 2B, for example), as previously described herein.

Figure 8A:
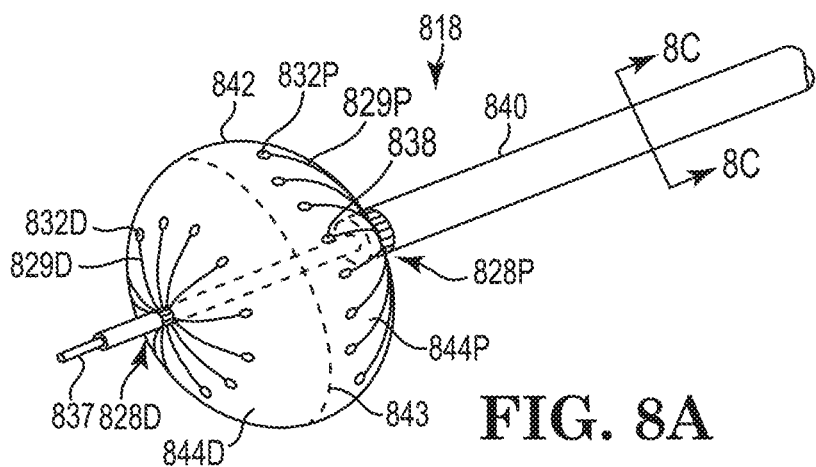
FIGS. 8A and 8B are perspective views of a portion of another embodiment of a cryogenic balloon catheter and a portion of a mapping assembly including a cryoballoon shown in an inflated state.
Figure 8B:
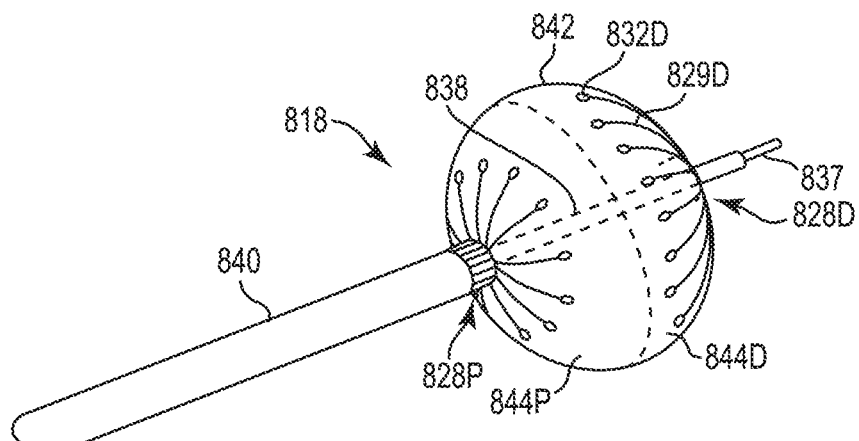

FIGS. 8A and 8B are perspective views of a portion of another embodiment of a cryogenic balloon catheter 818 having a proximal electrode array 828P and a distal electrode array 828D. As shown, and similar to the other balloon catheter embodiments described herein, the balloon catheter 818 includes a guidewire lumen 838 capable of receiving a guidewire 837, a catheter shaft 840 and a cryoballoon 842 mounted to the shaft 840 and the guidewire lumen 838. In the illustrated embodiment, the cryoballoon 842 is shown in an inflated state. It is understood that the balloon catheter 818 can include other structures as well that are not shown and/or described relative to FIGS. 8A or 8B.

In the illustrated embodiment, the proximal electrode array 828P includes a plurality of proximal electrodes 832P and respective conductor elements, e.g., flex circuits 829P associated therewith. Additionally, the distal electrode array 828D includes a plurality of distal electrodes 832D and respective conductor elements, e.g., flex circuits 829D associated therewith. In the illustrated embodiment, the proximal and distal electrode arrays 828P, 828D are electrically isolated from one another, as will be described in greater detail below. As such, the catheter 818 has no electrodes located along the maximum circumference 843/

In various embodiments, the proximal and distal electrode arrays 828P, 828D can be constructed substantially similar or the same as the electrode arrays described above in connection with other embodiments. For example, in embodiments, the individual proximal and distal electrodes 832P, 832D can be configured in the same manner as the electrode heads 231, 331 illustrated and described above in connection with FIGS. 2A and 3. Additionally, the electrode arrays 828P, 828D can be arranged so that the individual electrodes 832P, 832D define one or more planes such as in the balloon catheters 418, 518, 618 illustrated and described above.

As shown, the cryoballoon 842 includes a proximal cryoballoon region 844P and a distal cryoballoon region 844D. As used herein, the proximal cryoballoon region 844P includes the region where at least a portion of the cryoballoon 842 is secured or attached to a portion of the catheter shaft 840. Further, the distal cryoballoon region 844D includes the region where at least a portion of the cryoballoon 842 is secured or attached to the guidewire lumen 838. Alternatively, the proximal cryoballoon region 844P and/or the distal cryoballoon region 844D can be secured to other suitable structures within the catheter system 210. The proximal cryoballoon region 844P and/or the distal cryoballoon region 844D can be secured or attached to the guidewire lumen 838, the catheter shaft 840 and/or any other suitable structures, via any manner or method, such as with an adhesive or heat-bonding, as non-exclusive examples.

Additionally, in various embodiments, the cryoballoon 842 can include an inner surface and an opposed outer surface. The outer surface can include a proximal outer surface 842P and a distal outer surface 842D. The maximum circumference 843 delineates where the proximal outer surface 842P and the distal outer 842D meet. In other words, the maximum circumference 843 divides the outer surface. Furthermore, the inner surface can include a proximal inner surface (not shown) and a distal inner surface (not shown), which substantially corresponds with the proximal outer surface 842P and the distal outer surface 842D, respectively.

Figure 8C:
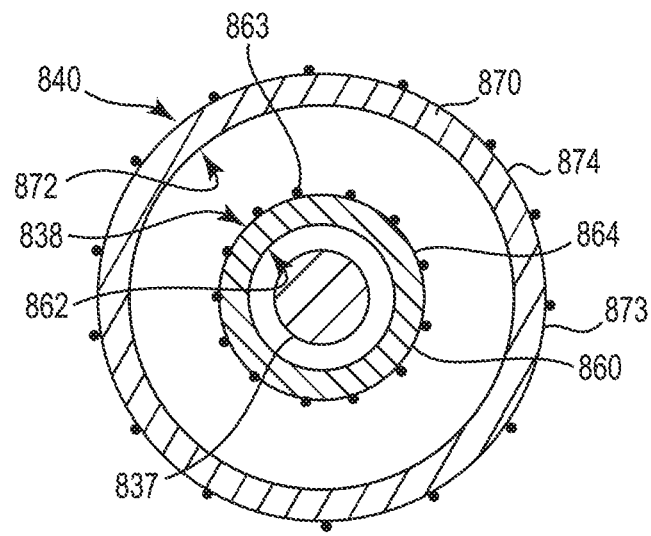
FIG. 8C is a cross-sectional view of a portion of the balloon catheter of FIGS. 8A-8B taken along the line 8C-8C in FIG. 8B.

FIG. 8C is a cross-sectional view of a portion of the cryogenic balloon catheter 818 taken along the line 8C-8C in FIG. 8B. As shown, the guidewire lumen 838 receives the guidewire 837 and has a guidewire lumen wall 860 defining a guidewire lumen inner surface 862 and a guidewire lumen outer surface 864. Additionally, the catheter shaft 840 has a shaft wall 870 defining a shaft inner surface 872 and a shaft outer surface 874. As further shown, the balloon catheter 818 includes a plurality of conductors 863 associated with the guidewire lumen 838, and a plurality of conductors 873 associated with the shaft 840.

Generally speaking, the conductors 863, 873 can extend or be routed from the handle assembly 20 (illustrated in FIG. 1) and/or the control system 14 to the electrode arrays 828P, 828D, respectively, and consequently, to the electrodes 832P, 832D. In various embodiments, at least a portion of the conductors 863 can extend or be routed on, through or within the guidewire lumen 838, and at least a portion of the conductors 873 can extend or be routed on, through or within the catheter shaft 840.

For example, in certain embodiments, such as the embodiment illustrated in FIG. 8C, a portion of the conductors 863 can be routed along the guidewire lumen outer surface 864 and operatively coupled to the electrodes 832D via the respective flex circuits 829D (see FIGS. 8A-8B) or comparable conductive elements. However, in other embodiments, portions of the conductors 863 could be routed along the guidewire lumen inner surface 862 or could be embedded within the guidewire lumen wall 860. In still other embodiments (not shown), the conductors 863 can be routed along or within a separate conductor lumen such as illustrated in FIG. 5D.

As further illustrated, in the embodiment of FIG. 8C the conductors 873 can be routed along the shaft outer surface 872 and operatively coupled to the electrodes 832P via the flex circuits 829P (see FIGS. 8A-8B) or comparable conductive elements. Similarly, in various embodiments, the conductors 873 can be routed along the shaft inner surface 872 or can be embedded within the shaft wall 870.

In various embodiments, the conductors 863, 873 may be separate conductors that are electrically bonded to the respective flex circuits 829D, 829P. Alternatively, in embodiments, the conductors 863, 873 may be integrally formed with the flex circuits 829D, 829P and/or the electrodes 832D, 832P, respectively, i.e., in a single structure extending from the cryoballoon 842 to the catheter handle. Additional variations of the conductors and flex circuits/electrodes will be apparent to those skilled in the art based on the foregoing.

The plurality of electrodes 832D, 832P can be configured to generate electrical signals, i.e., sensor output. The sensor output can include mapping information that may be provided to the operator so that the operator can identify the positioning of the cryoballoon 842 within the body of the patient 12. Furthermore, the sensor output can include one or more physiological parameters within the pulmonary vein, such as temperature, pressure or electrical potentials within the blood of the pulmonary vein. In one embodiment, the electrodes 832D, 832P are in electrical communication with the control system 14, via the plurality of conductors 234.

In this configuration, the electrodes 832D, 832P can come in direct contact with a portion of the circulatory system of the patient 12, i.e., the left atrium or other parts of the heart such as the ostium of the pulmonary vein, to better map and/or sense various physiological parameters that are occurring at or near the ostium. In alternative embodiments, the electrodes can be secured to the inner surface, i.e., the proximal inner surface and/or the distal inner surface of the cryoballoon 842.

During use in a cryoablation procedure, particularly a pulmonary vein isolation procedure in which the cryoballoon 842 operates to form a therapeutically effective lesion at or proximate the pulmonary vein ostium, the relative positions of the proximal and distal electrodes 832P, 832D can advantageously facilitate electrical on opposite sides of the lesion(s). That is, when the cryoballoon 842 is positioned so as to form the aforementioned lesion, the distal electrodes 832D may be positioned within the pulmonary vein upstream of the ostium, and the proximal electrodes 832P may be positioned within the left atrium on the opposite side of the lesion from the distal electrodes 832D. This arrangement can provide valuable information to the clinician as to the lesion's effectiveness in forming a conduction block. In embodiments, selected proximal and distal electrodes 832P, 832D may form electrode pairs for bi-polar sensing of the tissue between the electrodes, e.g., the necrosed tissue.

It is appreciated that the embodiments of the electrode array described in detail herein enable the realization of one or more advantages during the cryoablation procedure. With the various designs illustrated and described herein, the electrode array can provide more precise planar mapping of endocardial heart tissue. In utilizing the electrode array, near field and far field signals can be more readily distinguished, thus allowing for more clear and accurate tissue assessment within the boundaries of the electrodes on each flex circuit. This more precise mapping capability can further offer an enhanced ability to identify aberrant tissue, which then can be ablated without having to move and/or reposition the balloon catheter. Moreover, by comparing endocardial electrograms measured by each electrode, important physiological parameters can be measured and compared. For example, the temporal distribution of electrograms as measured on each electrode, and also from flex circuit to flex circuit, may help to determine the point of earliest activation. More specifically, by comparing the activation time on each electrode, the sequence or timing of the depolarization of the heart can be more effectively determined.

Additionally, the electrode array can assist in increasing a signal-to-noise ratio, which can allow for improved mapping capabilities while more effectively removing any noise.

Furthermore, the embodiments of the electrode array described herein can include devices and methods for selective application of electroporation therapy in a minimally invasive context while suppressing the generation of undesirable electrical discharge or breakdown. The embodiments described herein can result in well controlled and specific delivery of electroporation in a safer and more efficacious manner while preserving overall tissue integrity of the patient. Bi-polar configurations of electrodes, such as those described within, can be utilized to deliver short duration high voltage pulses intended to disturb cell membranes and result in cell apoptosis. The delivery of pulses can be controlled in sequential fashion both within the mapping head itself and from mapping head to mapping head. The precise spacing and electrode geometry of each mapping head ensuring a repeatable energy field density and control of the energy.

The inflatable balloon form can offer a clear view of inflatable balloon position within a heart chamber such as the left atrium, for example, to ensure the energy is delivered to the intended location. The arrays of electrodes enable more accurate and/or precise delivery of energy to the antral region of heart tissue outside the pulmonary veins in a wide, contiguous pattern due to the precisely repeating modular arrays of electrodes, which are mounted advantageously to provide an improved ablation pattern.

It is understood that although a number of different embodiments of the cryogenic balloon catheter system and the injection line compensation assembly have been illustrated and described herein, one or more features of any one embodiment can be combined with one or more features of one or more of the other embodiments, provided that such combination satisfies the intent of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A cryoablation catheter comprising:
   a catheter shaft;
   a guidewire lumen disposed within the catheter shaft;
   a conductor lumen disposed about the guidewire lumen within the catheter shaft;
   a cryoballoon having a distal end connected to the guidewire lumen and an opposite proximal end connected to the catheter shaft, the cryoballoon configured to transition between a deflated state and an inflated state, the cryoballoon having a maximum circumference in the inflated state;
   a proximal electrode array arranged around the cryoballon proximal to the maximum circumference, the proximal electrode array comprising a plurality of proximal flex circuits each having a plurality of proximal electrodes and a plurality of first conductors coupled to and proximally extending from the proximal electrodes, each proximal flex circuit having a distal end located proximally of the maximum circumference of the cryoballoon;
   wherein the proximal flex circuits are at least partially embedded within at least a portion of the catheter shaft and extend from the catheter shaft to the cryoballoon at the proximal end of the cryoballoon;
   a distal electrode array disposed around the cryoballoon distal to the maximum circumference, the distal electrode array comprising a plurality of distal flex circuits each having a plurality of distal electrodes and a plurality of second conductors electrically coupled to and distally extending distal from the distal electrodes, each distal flex circuit having a proximal end located distally of the maximum circumference of the cryoballoon; and wherein the distal flex circuits are routed within a wall defining the conductor lumen and extend from the catheter shaft to the cryoballoon at the distal end of the cryoballoon, wherein the cryoablation catheter has no proximal and distal electrodes and no proximal and distal flex circuits located at the maximum circumference of the cryoballoon.

2. The cryoablation catheter of claim 1, wherein each of the distal flex circuits includes at least three of the distal electrodes.

3. The cryoablation catheter of claim 2, wherein each of the distal flex circuits includes three of the distal electrodes arranged in a substantially triangular configuration.

4. The cryoablation catheter of claim 2, wherein each of the distal flex circuits includes four of the distal electrodes arranged in a substantially square configuration.

5. The cryoablation catheter of claim 2, wherein each of the proximal flex circuits includes at least three of the proximal electrodes.

6. The cryoablation catheter of claim 5, wherein each of the proximal flex circuits includes three of the proximal electrodes arranged in a substantially triangular configuration.

7. The cryoablation catheter of claim 5, wherein each of the proximal flex circuits includes four of the proximal electrodes arranged in a substantially square configuration.

8. A cryoablation catheter comprising:
a catheter shaft;
a guidewire lumen disposed within the catheter shaft;
a conductor lumen disposed about the guidewire lumen within the catheter shaft;
a cryoballoon having a distal end connected to the guidewire lumen and an opposite proximal end connected to the catheter shaft, the cryoballoon configured to transition between a deflated state and an inflated state, the cryoballoon having a maximum circumference in the inflated state;
a distal electrode array including a plurality of first flex circuits secured to the cryoballoon, each of the first flex circuits having a flex circuit proximal end located distally of the maximum circumference of the cryoballoon and including at least three spaced apart electrodes positioned substantially equidistant from one another;

the plurality of first flex circuits having a plurality of first conductors that are at least partially embedded within at least a portion of the catheter shaft and extend from the distal end of the cryoballoon, wherein the plurality of first flex circuits are arranged so that certain of the electrodes are disposed around the cryoballoon so as to define a first plane when the cryoballoon is in the inflated state, and certain other ones of the electrodes are disposed around the cryoballoon to define a second plane when the cryoballoon is in the inflated state, the first and second planes lying in a direction orthogonal to a longitudinal axis of the catheter shaft;

a proximal electrode array comprising a plurality of second flex circuits secured to the cryoballoon, each of the second flex circuits having a flex circuit distal end located proximally of the maximum circumference of the cryoballoon and including at least three spaced apart electrodes positioned substantially equidistant from one another; and the plurality of second flex circuit having a plurality of second conductors that are routed within a wall defining the conductor lumen and extend from the proximal end of the cryoballoon, wherein the plurality of second flex circuits are arranged so that certain of the electrodes of the plurality of second flex circuits are disposed around the cryoballoon so as to define a third plane when the cryoballoon is in the inflated state, and certain other ones of the electrodes of the plurality of second flex circuits are disposed around the cryoballoon to define a fourth plane when the cryoballoon is in the inflated state, the third and fourth planes lying in a direction orthogonal to a longitudinal axis of the catheter shaft, and wherein the cryoablation catheter has no electrodes and no proximal and distal flex circuits located at the maximum circumference of the cryoballoon.

9. The cryoablation catheter of claim 8, the electrodes of each first flex circuit are positioned in a substantially triangular configuration.

10. The cryoablation catheter of claim 8, wherein each of the first flex circuits includes four spaced apart electrodes arranged in a substantially square configuration.

11. The cryoablation catheter of claim 8, wherein the cryoballoon includes a proximal outer surface and a distal outer surface, and wherein the plurality of first flex circuits are secured to the distal outer surface of the cryoballoon.

* * * * *